US006379894B1

(12) United States Patent
Mach

(10) Patent No.: US 6,379,894 B1
(45) Date of Patent: Apr. 30, 2002

(54) METHOD FOR SCREENING COMPOUNDS CAPABLE OF INHIBITING BINDING BETWEEN THE TRANSCRIPTION FACTOR OF STAT1 AND THE TRANSCRIPTION FACTOR OF USF1

(75) Inventor: Bernard Mach, Chambésy (CH)

(73) Assignee: Novimaune S.A. (CH)

( * ) Notice: Subject to any disclaimer, the term of this patent is extended or adjusted under 35 U.S.C. 154(b) by 0 days.

(21) Appl. No.: 09/641,999

(22) Filed: Aug. 18, 2000

Related U.S. Application Data

(63) Continuation of application No. PCT/FR99/00376, filed on Feb. 19, 1999.

(30) Foreign Application Priority Data

Feb. 19, 1998 (FR) .............................................. 98 02025

(51) Int. Cl.⁷ .......................... C12Q 1/68; G01N 33/53; G01N 33/566
(52) U.S. Cl. .......................... 435/6; 435/7.1; 435/69.1; 435/70.1; 435/455; 436/501
(58) Field of Search ....................... 436/94, 501; 435/6, 435/7.1, 69.1, 70.1, 455

(56) References Cited

U.S. PATENT DOCUMENTS

| | | | | |
|---|---|---|---|---|
| 5,707,803 A | * | 1/1998 | Lamb et al. .................... | 435/6 |
| 5,731,155 A | * | 3/1998 | Schreiber et al. ............. | 435/7.1 |
| 5,814,517 A | * | 9/1998 | Seidel et al. ................. | 435/325 |
| 5,821,053 A | * | 10/1998 | Auron et al. .................... | 435/6 |
| 5,883,228 A | * | 3/1999 | Darnell, Jr. et al. ......... | 530/350 |
| 5,969,210 A | * | 10/1999 | Sharma et al. .................. | 800/3 |
| 6,124,118 A | * | 9/2000 | Darnell, Jr. et al. ........ | 435/69.1 |
| 6,207,391 B1 | * | 3/2001 | Wu et al. ..................... | 435/7.1 |
| 6,235,873 B1 | * | 5/2001 | Bromberg et al. ........... | 530/300 |

FOREIGN PATENT DOCUMENTS

| | | |
|---|---|---|
| EP | 0 648 836 A1 | 4/1995 |
| EP | 0 874 049 A1 | 10/1998 |
| FR | 97 04954 | 10/1998 |
| WO | 95/28482 | 10/1995 |
| WO | 95/28492 | 10/1995 |
| WO | 96/06107 | 2/1996 |
| WO | 96/15265 | 5/1996 |

OTHER PUBLICATIONS

Muhlethaler–Mottet, A., et al. "Activation of the MHC Class II Transactivator CIITA by Interferon–Gamma Requires Cooperative Interaction between Stat1 and USF–1." Immunity, (Feb. 1998) vol. 8, No. 2, pp. 157–166, XP002083358.
Muhlethaler–Mottet, A, et al. "Expression of MHC class II molecules in different cellular and functional compartments is controlled by differential usage of multiple promoters of the transactivator CIITA" EMBO Journal, vol. 16, No. 10, May 15, 1997, pp. 2851–2860, XP002051561.
Piskurich, J. F., et al. "Identification of Distinct Regions of 5' Flanking DNA That Mediate Constitutive, IFN–Gamma, STAT1, and TGF–Beta–Regulated Expression of the Class II Transactivator Gene" Journal of Immunology, vol. 160, No. 1, Jan. 1998, pp. 233–240, XP002073465.
Lennon, A–M., et al. "Isolation of a B–cell–specific promoter for the human class II transactivator" Immunogenetics, vol. 45, No. 4, 1997, pp. 266–273, XP002051562.
Piskurich, J.F., et al. "Two Distinct Gamma Interferon–Inducible Promoters of the Major Histocompatibility Complex Class II Transactivator Gene Are Differentially Regulated by STAT1, Interferon Regulatory Factor 1, and Transforming Growth Factor Beta" Molecular and Cellular Biology, (Jan. 1999), vol. 19, No. 1, pp. 431–440, XP002108509.
Bottazzo, G. F., et al. "Organ–Specific Autoimmunity: A 1986 Overview" Immunological Reviews 1986, No. 94, pp. 137–169.
Mach, B., et al. "Regulation of MHC Class II Genes: Lessons from a Disease" Annu. Rev. Immunol. 1996, vol. 14, pp. 301–331.
Steimle, V., et al. "Complementation Cloning of an MHC Class II Transactivator Mutated in Hereditary MHC Class II Deficiency (or Bare Lymphocyte Syndrome)" CELL, vol. 75, Oct. 8, 1993, pp. 135–146, XP002051559.
Cogswell, Ph.D., J.P., et al. "Transcriptional Regulation of the HLA–DRA Gene" Critical Reviews in Immunology, vol. 11, No. 2, 1991, pp. 87–112.
Silacci, P., et al. "Developmental Extinction of Major Histocompatibility Complex Class II Gene Expression in Plasmocytes Is Mediated by Silencing of the Transactivator Gene CIITA" J. Exp. Med., vol. 180, Oct. 1994, pp. 1329–1336.
Darnell, Jr., J. E. "STATs and Gene Regulation", SCIENCE, vol. 277, Sep. 12, 1997, pp. 1630–1635.
Chang, C–H., et al. "Class II Transactivator (CIITA) Is Sufficient for the Inducible Expression of Major Histocompatibility Complex Class II Genes" J. Exp. Med., vol. 180, Oct. 1994, pp. 1367–1374.

(List continued on next page.)

Primary Examiner—Kenneth R. Horlick
(74) Attorney, Agent, or Firm—Lerner, David, Littenberg, Krumholz & Mentlik, LLP

(57) ABSTRACT

The invention concerns a method for determining whether a candidate compound is capable of inhibiting fixing between STAT1 and USF1 polypeptides comprising the following steps: (a) provide all or part of the STAT1 polypeptide capable of fixing with the USF1 polypeptide; (b) providing all or part of the USF1 polypeptide capable of fixing with the STAT1 polypeptide; (c) contacting said polypeptides as defined in (a) and (b) with one said candidate compound in conditions suitable for fixing between STAT1 and USF1 polypeptides; (d) measuring the fixing between the STAT1 and USF1 polypeptides; and (e) comparing said measurement with the fixing measurement between STAT1 and USF1 polypeptides in similar experimental conditions in the absence of said candidate compound, a decrease in fixing leading to conclude that said compound candidate is capable of inhibiting fixing between STAT1 and USF1 polypeptides.

15 Claims, 1 Drawing Sheet

OTHER PUBLICATIONS

Meraz, M.A., et al. "Targeted Disruption of the Stat1 Gene in Mice Reveals Unexpected Physiologic Specificity in the JAK–STAT Signaling Pathway" Cell, vol. 84, Feb. 9, 1996, pp. 431–442.

Lee, Y–J. and Benveniste, E. N. "Stat1 Alpha Expression Is Involved in IFN–Gamma Induction of the Class II Transactivator and Class II MHC Genes" Journal of Immunology vol. 157, 1996, pp. 1559–1568.

Gregor, P. D., et al. "The sdenovirus major late transcription factor USF is a member of the helix–loop–helix group of regulatory proteins and binds to DNA as dimer" Genes & Development, vol. 4, 1990, pp. 1730–1740.

Beckmann, H., et al. "TFE3: A helix–loop–helix protein that activates transcription through the immunoglobulin enhancer $\mu$E3 motif" Genes & Development, vol. 4, 1990, pp. 167–179.

Sirito, M., et al. "Ubiquitous expression of the 43–and 44kDa forms of transcription factor USF in mammalian cells", Nucleic Acids Research, 1994, vol. 22, No. 3, pp. 427–433.

Ayer, D. E., et al. "Mad: A Heterodimeric Partner for Max That Antagonizes Myc Transcriptional Activity" Cell, vol. 72, Jan. 29, 1993, pp. 211–222.

Peritz, L. N., et al. "The Human Growth Hormone Gene Contains Both Positive and Negative Control Elements" Journal of Biological Chemistry, vol. 263, No. 11, 1988, pp. 5005–5007.

Chang, L.A., et al. "Identification of USF as the ubiquitous murine factor that binds to and stimulates transcription from the immunoglobulin $\lambda$2–chain promoter" Nucleic Acids Research, 1992, vol. 20, No. 2, pp. 287–293.

Reisman, D. and Rotter, V. "The helix–loop–helix containing transcription factor USF binds to and transactivates the promoter of the p53 tumor suppressor gene" Nucleic Acids Research, 1993, vol. 21, No. 2, pp. 345–350.

Greenlund, A. C., et al. "Stat Recruitment by Tyrosine–Phosphorylated Cytokine Receptors: An Ordered Reversible Affinity–Driven Process" Immunity, vol. 2, Jun. 1995, pp. 677–687.

Roy, A. L., et al., "Cooperative interaction of an initiator–binding transcription initiation factor and the helix–loop–helix activator USF" Nature, vol. 354, Nov. 21, 1991, pp. 245–248.

Sperisen, P., et al. "A PCR–based Assay for Reporter Gene Expression", PCR Methods and Applications, vol. 1, 1992, pp. 164–170.

Harroch, S., et al. "Induction by interleukin–6 of interferon regulatory factor 1 (IRF–1) gene expression through the palindromic interferon response element pIRE and cell type–dependent control of IRF–1 binding to DNA" EMBO Journal, vol. 13, No. 8, 1994, pp. 1942–1949.

Decker, T., et al. "Cytoplasmic activation of GAF, an IFN-–Gamma–regulated DNA–binding factor" EMBO Journal, vol. 10, No. 4, 1991, pp. 927–932.

* cited by examiner

FIG. 1

GGGGAGAAGTCAGAGGTAACCTTGCCCCCTCCCTCAATTCCAGATGAGGAAATTCAGGCC
TGAAAAGGGAAAGTGACCACCTCAAAGTCTCATGCCTTGGAGGACCCAGCAGGAATCCAA
GACCTCTGAAAAGGACCGGCAGGGCTCTTGCCACGGCTGGGGGTGTGGTCATGGTAACAC
AGGTTTTCCATCCATGGAAGGTACCTGAGGGATTTTCTCTTCCTCCCTAGGGCCAGCATC
AGAGGAGTGAATAGCTCAGTTAGCTCATCTCAGGGGCCATGTGCCCTCGGAGGTGGTTTG
CCACTTTCACGGTTGGACTGAGTTGGAGAGAAACAGAGACCCACCCAGGGGTGGGGACAA
GCTCCCTGCAACTCAGGACTTGCAGATCACTTGCCCAAGTGGCTCCCTAGCTCCTGGCTC

NfκB
CTGGCCCGGGGCCT|GGGACTCTCC|CCGAAGTGGGGCTGGCCACTGTGAGGAACCGACTGG

NFGMa      GAS      Ebox
AGGCAGGGACCTCTTGGATGCCCCAGGCAGTT|GGGATGCCAC|TTCTGATAAAG|CACGTG|G

TGGCCACAGTAGGTGCTTGGTTGCTCCACAGCCTGGCCCGAGCTCAGCGCTGCAGAAA|GA

IRF1/2
|AAGTGAAAGG|GAAAAAGAACTGCGGGGAGGCGGGGAGGTAGGATGACCAGCGGACGAGCT

+1
GCCACAGACTTGCCGCGGCCCCAGAGCTGGCGGGAGGGAGAGGCCACCAGCAGCGCGCGC
GGGAGCCCGGGGAACAGCGGCAGCTCACAGTGTGCCACCATG (SEQ ID NO:6)

SEQUENCE LISTING

<160> NUMBER OF SEQ ID NOS: 6

<210> SEQ ID NO 1
<211> LENGTH: 664
<212> TYPE: DNA
<213> ORGANISM: Homo sapiens

<400> SEQUENCE: 1

```
ggggagaagt cagaggtaac cttgccccct ccctcaattc cagatgagga aattcaggcc    60
tgaaaaggga aagtgaccac ctcaaagtct catgccttgg aggacccagc aggaatccaa   120
gacctctgaa aaggaccggc agggctcttg ccacggctgg gggtgtggtc atggtaacac   180
aggttttcca tccatggaag gtacctgagg gattttctct tcctccctag ggccagcatc   240
agaggagtga atagctcagt tagctcatct caggggccat gtgccctcgg aggtggtttg   300
ccactttcac ggttggactg agttggagag aaacagagac ccacccaggg gtggggacaa   360
gctccctgca actcaggact tgcagatcac ttgcccaagt ggctccctag ctcctggctc   420
ctggcccggg gcctgggact ctccccgaag tggggctggc cactgtgagg aaccgactgg   480
aggcagggac ctcttggatg ccccaggcag ttgggatgcc acttctgata aagcacgtgg   540
tggccacagt aggtgcttgg ttgctccaca gcctggcccg agctcagcgc tgcagaaaga   600
aagtgaaagg gaaaagaac tgcggggagg cggggaggta ggatgaccag cggacgagct   660
gcca                                                                664
```

<210> SEQ ID NO 2
<211> LENGTH: 4441
<212> TYPE: DNA
<213> ORGANISM: Homo sapiens

<400> SEQUENCE: 2

```
cagacttgcc gcggccccag agctggcggg agggagaggc caccagcagc gcgcgcggga    60
gcccggggaa cagcggcagc tcacagtgtg ccaccatgga gttggggccc ctagaaggtg   120
gctacctgga gcttcttaac agcgatgctg accccctgtg cctctaccac ttctatgacc   180
agatggacct ggctggagaa gaagagattg agctctactc agaacccgac acagacacca   240
tcaactgcga ccagttcagc aggctgtttg tgtgacatgga aggtgatgaa gagaccaggg   300
aggcttatgc caatatcgcg gaactggacc agtatgtctt ccaggactcc cagctggagg   360
gcctgagcaa ggacattttc aagcacatag gaccagatga agtgatcggt gagagtatgg   420
agatgccagc agaagttggg cagaaaagtc agaaaagacc cttcccagag gagcttccgg   480
cagacctgaa gcactggaag ccagctgagc cccccactgt ggtgactggc agtctcctag   540
tgggaccagt gagcgactgc tccacccctgc cctgcctgcc actgcctgcg ctgttcaacc   600
aggagccagc ctccggccag atgcgcctgg agaaaaccga ccagattccc atgcctttct   660
ccagttcctc gttgagctgc ctgaatctcc ctgagggacc catccagttt gtccccacca   720
tctccactct gccccatggg ctctggcaaa tctctgaggc tggaacaggg gtctccagta   780
tattcatcta ccatggtgag gtgccccagg ccagccaagt accccctccc agtggattca   840
ctgtccacgg cctcccaaca tctccagacc ggccaggctc caccagcccc ttcgctccat   900
cagccactga cctgcccagc atgcctgaac ctgccctgac ctcccgagca acatgacag   960
agcacaagac gtccccacc caatgcccgg cagctggaga ggtctccaac aagcttccaa  1020
aatggccctga gccggtggag cagttctacc gctcactgca ggacacgtat ggtgccgagc  1080
```

-continued

```
ccgcaggccc ggatggcatc ctagtggagg tggatctggt gcaggccagg ctggagagga    1140
gcagcagcaa gagcctggag cgggaactgg ccaccccgga ctgggcagaa cggcagctgg    1200
cccaaggagg cctggctgag gtgctgttgg ctgccaagga gcaccggcgg ccgcgtgaga    1260
cacgagtgat tgctgtgctg ggcaaagctg tcagggcaa gagctattgg gctggggcag     1320
tgagccgggc ctgggcttgt ggccggcttc cccagtacga ctttgtcttc tctgtcccct    1380
gccattgctt gaaccgtccg ggggatgcct atggcctgca ggatctgctc ttctccctgg    1440
gcccacagcc actcgtggcg ccgatgagg ttttcagcca catcttgaag agacctgacc     1500
gcgttctgct catcctagac gccttcgagg agctggaagc gcaagatggc ttcctgcaca    1560
gcacgtgcgg accggcaccg gcggagccct gctccctccg ggggctgctg gccggccttt    1620
tccagaagaa gctgctccga ggttgcaccc tcctcctcac agcccggccc cggggccgcc    1680
tggtccagag cctgagcaag gccgacgccc tatttgagct gtccggcttc tccatggagc    1740
aggcccaggc atacgtgatg cgctactttg agagctcagg gatgacagag caccaagaca    1800
gagccctgac gctcctccgg gaccggccac ttcttctcag tcacagccac agccctactt    1860
tgtgccgggc agtgtgccag ctctcagagg ccctgctgga gcttggggag gacgccaagc    1920
tgccctccac gctcacggga ctctatgtcg gcctgctggg ccgtgcagcc ctcgacagcc    1980
cccccggggc cctggcagag ctggccaagc tggcctggga gctgggccgc agacatcaaa    2040
gtaccctaca ggaggaccag ttcccatccg cagacgtgag gacctgggcg atggccaaag    2100
gcttagtcca acacccaccg cgggccgcag agtccgagct ggccttcccc agcttcctcc    2160
tgcaatgctt cctgggggcc ctgtggctgg ctctgagtgg cgaaatcaag gacaaggagc    2220
tcccgcagta cctagcattg accccaagga agaagaggcc ctatgacaac tggctggagg    2280
gcgtgccacg ctttctggct gggctgatct tccagcctcc cgcccgctgc ctgggagccc    2340
tactcgggcc atcggcggct gcctcggtgg acaggaagca gaaggtgctt gcgaggtacc    2400
tgaagcggct gcagccgggg acactgcggg cgcggcagct gcttgagctg ctgcactgcg    2460
cccacgaggc cgaggaggct ggaatttggc agcacgtggt acaggagctc cccggccgcc    2520
tctcttttct gggcacccgc ctcacgcctc ctgatgcaca tgtactgggc aaggccttgg    2580
aggcggcggg ccaagacttc tccctggacc tccgcagcac tggcatttgc ccctctggat    2640
tggggagcct cgtgggactc agctgtgtca cccgtttcag ggctgccttg agcgacacgg    2700
tggcgctgtg ggagtccctg cggcagcatg gggagaccaa gctacttcag gcagcagagg    2760
agaagttcac catcgagcct ttcaaagcca agtccctgaa ggatgtggaa gacctgggaa    2820
agcttgtgca gactcagagg acgagaagtt cctcggaaga cacagctggg gagctccctg    2880
ctgttcggga cctaaagaaa ctggagtttg cgctgggccc tgtctcaggc ccccaggctt    2940
tccccaaact ggtgcggatc ctcacggcct tttcctccct gcagcatctg gacctggatg    3000
cgctgagtga gaacaagatc ggggacgagg gtgtctcgca gctctcagcc accttccccc    3060
agctgaagtc cttggaaacc ctcaatctgt cccagaacaa catcactgac ctgggtgcct    3120
acaaactcgc cgaggccctg ccttcgctcg ctgcatccct gctcaggcta agcttgtaca    3180
ataactgcat ctgcgacgtg ggagccgaga gcttggctcg tgtgcttccg gacatggtgt    3240
ccctccgggt gatggacgca agttcacggc tgccggggcc cagcagctcg ctgccagcct    3300
tcggaggtgt cctcatgtgg agacgctggc gatgtggacg cccaccatcc cattcagtgt    3360
ccaggaacac ctgcaacaac aggattcacg gatcagcctg agatgatccc agctgtgctc    3420
```

```
tggacaggca tgttctctga ggacactaac cacgctggac cttgaactgg gtacttgtgg    3480
acacagctct tctccaggct gtatcccatg aggcctcagc atcctggcac ccggcccctg    3540
ctggttcagg gttggcccct gcccggctgc ggaatgaacc acatcttgct ctgctgacag    3600
acacaggccc ggctccaggc tcctttagcg cccagttggg tggatgcctg gtggcagctg    3660
cggtccaccc aggagccccg aggccttctc tgaaggacat tgcggacagc cacggccagg    3720
ccagagggag tgacagaggc agccccattc tgcctgccca ggcccctgcc accctgggga    3780
gaaagtactt cttttttttt attttagac agagtctcac tgttgcccag gctgcgtgc     3840 agtggtgcga tctgggttca ctgcaacctc cgcctcttgg gttcaagcga ttcttctgct    3900
tcagcctccc gagtagctgg gactacaggc acccaccatc atgtctggct aattttcat    3960 ttttagtaga cacagggttt tgccatgttg gccaggctgg tctcaaactc ttgacctcag    4020
gtgatccacc cacctcagcc tcccaaagtg ctggggatta caagcgtgag ccactgcacc    4080
gggccacaga gaaagtactt ctccaccctg ctctccgacc agacaccttg acagggcaca    4140
ccgggcactc agaagacact gatgggcaac ccccagcctg ctaattcccc agattgcaac    4200
aggctgggct tcagtggcag gctgcttttg tctatggac tcaatgcact gacattgttg     4260
gccaaagcca aagctaggcc tggccagatg caccaggccc ttagcaggga acagctaat     4320 gggacactaa tggggcggtg agaggggaac agactggaag cacagcttca tttcctgtgt    4380
cttttttcac tacattataa atgtctcttt aatgtcacaa aaaaaaaaaa aaaaaaaaa     4440 a                                                                    4441
```

<210> SEQ ID NO 3
<211> LENGTH: 10
<212> TYPE: DNA
<213> ORGANISM: Unknown Organism
<220> FEATURE:
<223> OTHER INFORMATION: Description of Unknown Organism: GAS element

<400> SEQUENCE: 3

```
ttctgataaa                                                              10
```

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence:
     oligonucleotide

<400> SEQUENCE: 4

```
ggccagggat tgggatgcga gttctgataa agcaggtggt ggccacag                    48
```

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:
     oligonucleotide

<400> SEQUENCE: 5

```
gggaaagcac gtcctggcc                                                    19
```

<210> SEQ ID NO 6
<211> LENGTH: 762
<212> TYPE: DNA
<213> ORGANISM: Homo sapiens -continued

```
<400> SEQUENCE: 6
ggggagaagt cagaggtaac cttgccccct ccctcaattc cagatgagga aattcaggcc     60
tgaaaaggga aagtgaccac ctcaaagtct catgccttgg aggacccagc aggaatccaa    120
gacctctgaa aaggaccggc agggctcttg ccacggctgg gggtgtggtc atggtaacac    180
aggttttcca tccatggaag gtacctgagg gattttctct tcctccctag ggccagcatc    240
agaggagtga atagctcagt tagctcatct caggggccat gtgccctcgg aggtggtttg    300
ccactttcac ggttggactg agttggagag aaacagagac ccacccaggg gtggggacaa    360
gctccctgca actcaggact tgcagatcac ttgcccaagt ggctccctag ctcctggctc    420
ctggcccggg gcctgggact ctccccgaag tggggctggc cactgtgagg aaccgactgg    480
aggcagggac ctcttggatg ccccaggcag ttgggatgcc acttctgata aagcacgtgg    540
tggccacagt aggtgcttgg ttgctccaca gcctggcccg agctcagcgc tgcagaaaga    600
aagtgaaagg gaaaaagaac tgcggggagg cggggaggta ggatgaccag cggacgagct    660
gccacagact tgccgcggcc ccagagctgg cgggagggag aggccaccag cagcgcgcgc    720
gggagcccgg ggaacagcgg cagctcacag tgtgccacca tg                      762
```

METHOD FOR SCREENING COMPOUNDS CAPABLE OF INHIBITING BINDING BETWEEN THE TRANSCRIPTION FACTOR OF STAT1 AND THE TRANSCRIPTION FACTOR OF USF1

This application is a continuation of international application No. PCT/FR99/00376, filed Feb. 19, 1999, which claims priority on the basis of French Pat. Application No. 98/02025, filed Feb. 19, 1998.

BACKGROUND OF THE INVENTION

The present invention relates to a method for identifying compounds capable of inhibiting activation by cytokines, in particular by interferon γ, of expression of the CIITA gene which itself is involved in controlling and regulating the expression of genes coding for MHC class II molecules.

Molecules of the major histocompatibility complex (hereinafter designated MHC) class II are transmembrane heterodimeric glycoproteins which are directly involved in the activation of CD4+ T helper lymphocytes during the immune response.

In man, this class II complex is represented by molecules belonging to the HLA (human leukocyte antigen) system. Genes coding for the α and β chains constituting the HLA-DR, HLA-DQ and HLA-DP molecules are located in region D of chromosome 6.

Expression of these genes is perfectly regulated. In contrast to genes coding for MHC class I molecules which are expressed ubiquitously, the genes coding for MHC class II molecules are expressed either constitutively uniquely in some cell types such as B lymphocytes, activated T lymphocytes, macrophages, thymic epithelium cells, or dentritic cells such as Langerhans cells, or inductively after stimulation, for example by cytokines, and more particularly by interferon γ (INF γ) or interleukin 4 (IL4), in several other cell types such as cells from the macrophage or monocyte line, endothelial cells, fibroblasts, muscle cells or cancer cells such as melanoma cells.

Further, in B lymphocytes, the expression of genes coding for MHC class II molecules is transitory. Differentiation of B cells into plasmocytes producing immunoglobulins is accompanied by extinction of certain genes, including those coding for MHC class II.

Similarly, it has been shown that the amount of expression of MHC class II molecules constitutes a determining factor in the T cell activation process.

As a result, it is clear that molecular mechanisms for regulating the expression of these genes constitute a key element in the effectiveness of the immune response. Any defect in this regulation process can result in substantial immunological problems, or autoimmune diseases. Thus in some cases, abnormal expression of MHC class II genes has been observed on the surface of cells which normally should not express such genes. Similarly, an over-expression of these genes can be observed, leading to aberrant and uncontrolled activation of CD4+ lymphocytes (BOTTAZZO et al., 1986, Immunol. Rev., 94, 137–169). Such manifestations could be at least partially responsible for diseases such as insulin dependent diabetes, multiple sclerosis, rheumatoid arthritis or lupus erythematosus. In contrast, in some patients immunodeficiency has been demonstrated resulting from problems with expression of MHC class II genes. An example which can be cited is BLS syndrome (bare lymphocyte syndrome), which is a recessive autosomal disease in which expression of MHC class II genes is very limited or even non-existent, resulting in an absence of cellular and humoral immune response and accompanied by numerous infections which are often fatal.

A number of scientific teams have analysed the mechanisms of regulation of MHC class II gene expression and have identified a certain number of transactivating molecules which can directly or indirectly bind to specific promoter sequences of said genes (for a review, see MACH et al., 1996, Annu. Rev. Immunol. 14, 301–331).

The Applicant has previously identified and characterized one of these factors, the CIITA factor (class II transactivator) [STEIMLE et al., 1993, Cell 75, 135–146 and EP-A-0 648 836]. Further, International patent application WO-A-9606107 has shown that there are two domains in the CIITA factor which are more involved in activation of transcription of MHC class II genes. However, surprisingly and in contrast to that which has been observed for the other factors involved in regulating the expression of MHC class II genes [COGSWELL et al., 1991, Crit. Rev. Immunol. 11, 87–112], STEIMLE et al have shown that expression of the CIITA factor coincides closely with expression of MHC class II genes and is absolutely required both for constitutive expression and for induction of said MHC genes. Further, SILACCI et al (1994, J. Exp. Med., 180, 1329–1336) have shown that extinction of MHC class II genes during differentiation of plasmocytes is associated with extinction of the gene coding for the CIITA factor.

Further, LENNON et al (1997, Immunogenetics, 45, 266–273) have identified the promoter sequence of a CIITA gene which is responsible for differential expression of this factor in B cells. However, the existence of this single sequence does not explain why differential expression of the CIITA factor is observed in different cell types. Further, it does not account for induction by cytokines.

In previous studies, the Applicant used samples from different tissues of human origin to identify the complex organisation of sequences providing control of expression of the CIITA factor, the Applicant isolated and characterized several promoter regions and the Applicant demonstrated the existence of different forms of the CIITA factor and also different CIITA genes. These studies have formed the basis of a publication (MUHLETHALER-MOTTET et al., 1997, EMBO J., 16, 2851–2860) and form the subject matter of French patent application 97/04954 the contents of which are hereby incorporated into the present application. The inventors have thus shown that the different promoters identified can be activated selectively: two of the promoters are responsible for constitutive expression of the CIITA gene in dendritic cells (promoter I) and in B lymphocytes (promoter III) while promoter IV is involved in expressing the CIITA gene after induction by a cytokine, in particular interferon γ.

More particularly, the inventors have identified a sequence capable of expressing a transcriptional promoter activity after induction by a cytokine, such as interferon γ or interleukin 4. Such a sequence is represented by the sequence comprising all or part of a sequence identified as SEQ ID NO:1 (set forth on Table 1), or its complementary sequence. An analysis of this sequence has identified several regions corresponding to cis acting regulation expression sites, such as the NF-GMa site, the GAS element, the E-box or the IRF-1 factor binding site (MUHLETHALER-MOTTET et al, 1997, EMBO J., 16, 2851–2860 and FIG. 1).

More recently, a number of studies have provided a deeper understanding of the succession of events and signals involved in activating genes expressed in response to induction by a cytokine, in particular by interferon γ. An activation scheme has been proposed by DARNELL, (1997, Science 277, 1630–1635). In that model, firstly the activating cytokine, for example interferon γ, binds to its surface cell receptors thus enabling activation of cellular tyrosine kinases JAK1 and JAK2. Then the tyrosine residues of the STAT1 transcription factor, located in the cell cytoplasm, are phosphorylated by activated JAK kinases. This phosphorylation then enables the activated STAT1 factor to migrate into the nucleus where it binds to the GAS box of promoters inducible by cytokines (for example interferon γ) thus enabling activated expression of genes under the control of such promoters.

The implication of such a JAK/STAT1 activation system in the control of expression of CIITA genes inducible by interferon γ has been the subject of studies which have established that, as with other genes which are inducible by interferon γ, expression of the CIITA factor cannot be induced in cell lines which are deficient for JAK1 (CHANG et al., 1994, J. Exp. Med., 180, 1367–1374).

Similarly, MERAZ et al. (1996, Cell, 84, 431–442) have shown that CIITA gene expression is not induced by interferon Y in bone marrow macrophages from the STAT1$^{-/-}$ mouse, suggesting a determining role for STAT1 in inducing the expression of the CIITA gene by interferon γ.

Further, LEE and BENVENISTE (1996, J. Immunol. 157, 1559–1568) have carried out experiments using antisense oligonucleotides specific for the nucleic acid sequence coding for the STAT1 protein factor to demonstrate that the reduction in the expression of the STAT1 protein is accompanied by a reduction in the expression of the CIITA gene which can be observed after induction by interferon γ.

Finally, it has been shown that the STAT1 factor specifically recognises a particular nucleic acid sequence known as the "GAS element" (DARNELL, 1997, Science 277, 1630–1635). An analysis of the promoter IV sequence of the CIITA gene (inducible by cytokines: MUHLETHALER-MOTTET et al., 1997, EMBO J. 16, 2851–2860—and FIG. 1) has revealed the presence of such a sequence.

As has been described above, promoter IV also comprises the CACGTG sequence (E-box, GREGOR et al., 1990, Genes Dev., 4, 1730–1740, see FIG. 1). This could indicate that a transcription factor belonging to the helix/loop/helix/ leucine zipper family may intervene in regulating the expression of genes placed under the control of promoter IV. A number of factors from this family have been described in the literature, in particular constitutively expressed transcription factors such as TFE3 factors (BECKMANN et al., 1990, Genes Dev., 4, 167–179), USF1 (GREGOR et al., 1990, Genes Dev., 4, 1730–1740) and USF 2 (SIRITO et al., 1994, Nucleic Acid Res., 22, 427–433) or proteins involved in the Myc system such as Myc-Max or Mad-Max (AYER et al., 1993, Cell 72, 211–222).

More particularly, the USF1 transcription factor is expressed ubiquitously and participates in regulating the expression of different genes, certain of which are expressed in a "tissue specific" manner or in an inducible manner, for example the gene coding for the human growth hormone (PERITZ et al., 1988, J. Biol. Chem., 263, 5005–5007), the gene coding for the λ2 chain of immunoglobulins (CHANG et al., 1992, Nucleic Acid Res., 20, 287–293) or the gene coding for p53 (REISMAN and ROTTER, 1993, Nucleic Acid Res., 21, 345–350).

SUMMARY OF THE INVENTION

The Applicant has now demonstrated that STAT1 and USF1 transcription factors respectively bind to the GAS element and to the E-box of promoter IV. However, highly surprisingly, the Applicant has also demonstrated that binding of the STAT1 factor to the GAS site is greatly stabilized by the USF1 factor and that these factors are co-operatively bound to the binding sites located on promoter IV, this co-operative interaction playing a deciding role in controlling the specific activation of promoter IV by cytokines, in particular by interferon γ.

The expression "co-operatively bound" means that there is an interaction between the protein factors in question, which may take place before or after binding to their respective site, which can define specific interaction sites between said protein factors and which result in a co-operative effect. This co-operative effect is a result which can only be observed when the interaction in question takes place; for example this co-operative effect will consist in stabilizing binding of at least one of the protein factors to its site (it being understood that this is because of the interaction existing between the protein factors). In one particular case, the co-operative effect is a synergistic effect characterized in that the effect observed using the protein factors is more than the expected effect corresponding to the sum of the individual effects observed for each of the factors.

This mechanism for inducing expression of a gene placed under the control of promoter IV is distinguished from other systems previously described for genes inducible by interferon y in that this requires the USF1 factor as an essential partner for binding and as a result for the activity of the STAT1 factor. The discovery of this mechanism, in particular involved in activating the expression of the CIITA gene by interferon γ, and as a result in inducing MHC class II molecules by interferon γ, has led the Applicant to develop a novel method for identifying molecules which are capable of inhibiting the expression of genes placed under the control of a promoter the activity of which is induced by co-operative binding of STAT1 and USF1, and more particularly under the control of all or a portion of promoter IV. Preferably, said gene is the gene coding for CIITA.

The term "nucleic acid sequence coding for the CIITA polypeptide" means the sequence in question comprises all or a portion of a nucleic acid sequence corresponding to mRNA from different tissues or cell lines expressing a CIITA activity in a constitutive manner or after induction. Thus they can be at least partially coding sequences or, for example, sequences involved in controlling expression, in particular sequences with a transcriptional promoter activity.

The term "nucleic acid sequence" means a fragment of DNA and/or RNA, double or single stranded, isolated naturally occurring, or synthetic, forming a precise concatenation of modified or non modified nucleotides, which defines a fragment or a region of a nucleic acid.

The term "polypeptide" means a precise natural, isolated or synthesized, modified or non modified concatenation of amino acids, independent of its size or function.

The term "nucleic acid sequence with a transcriptional promoter activity" means a nucleic acid sequence which can control i.e., initiate and/or modulate, transcription of at least one homologous or heterologous gene located downstream of said sequence. Similarly, the promoter function of said sequences or promoter will be mentioned.

The term "reporter gene" means any nucleic acid sequence located downstream of a second nucleic acid sequence, permitting the analysis of the transcriptional promoter activity of said second sequence. In effect, transcription of that reporter gene results in the appearance of a product (RNA or polypeptide) which is readily detectable using well known conventional techniques.

The term "STAT1 transcription factor or polypeptide" means the STAT1 transcription factor which is capable of binding to the GAS element of promoters which are inducible by interferon γ (DARNELL, 1997, Science 277, 1630–1635).

The term "USF1 transcription factor or polypeptide" means the USF1 transcription factor which is capable of binding to the E-box of promoters such as the promoter of the gene coding for human growth hormone (PERITZ et al., 1988, J. Biol. Chem. 263, 5005–5007), the gene coding for the immunoglobulin λ2 chain (CHANG et al., 1992, Nucleic Acid Res., 20, 287–293) or the gene coding for p53 (REISMAN and ROTTER, 1993, Nucleic Acid Res., 21, 345–350).

It should also be mentioned that said STAT1 and USF1 factors can be recombinant or natural in origin, and more particularly consist of factors available in cell extracts, in particular nuclear extracts, prepared from cell lines, possibly stimulated by a cytokine, in particular interferon γ, expressing said factors. More particularly regarding the STAT1 factor, this can be either in a non activated form (non phosphorylated) or in an activated form (phosphorylated, in particular by the action of the JAK1 enzyme). Within the context of the present invention, the activated form of STAT1 is preferably selected.

BRIEF DESCRIPTION OF THE FIGURE

FIG. 1 is a sequence (designated as SEQ ID NO:6) of the different elements involved in regulating the expression induced by cytokines of genes placed under the control of promoter IV.

DETAILED DESCRIPTION

In a first aspect, the present invention provides a method for determining whether a candidate compound is capable of inhibiting binding between STAT1 and USF1 polypeptides, comprising the following steps:

(a) providing all or a portion of the STAT1 polypeptide having the property of binding to the USF1 polypeptide;

(b) providing all or a portion of the USF1 polypeptide having the property of binding to the STAT1 polypeptide;

(c) bringing said polypeptides as defined in a) and b) into contact with said candidate compound under conditions which enable binding between the STAT1 and USF1 polypeptides;

(d) measuring the binding between the STAT1 and USF1 polypeptides; and (e) comparing this measurement with that for binding between STAT1 and USF1 polypeptides observed under the same experimental conditions in the absence of said candidate compound, a reduction in binding allowing the conclusion that said candidate compound is capable of inhibiting binding between STAT1 and USF1 polypeptides.

The STATS and USF1 polypeptides used in the present invention can be either natural polypeptides extracted, for example, from cell lines expressing the corresponding genes, such as the Me67.8 line, and more particularly present in the nuclear extract of these lines, said lines optionally being stimulated by interferon γ, or recombinant proteins (GREENLUND et al., 1995, Immunity, 2, 677–687 for STAT1 and ROY et al, 1991, Nature 354, 245–248 for USF1). The preparation of nuclear extracts from cells is a technique which is well understood by the skilled person. The STAT1 and USF1 polypeptides used in the present invention may or may not preserve their activating function for other genes for which the co-operative effect of the two polypeptides has not been observed (the polypeptides thus act separately). More particularly, it is possible to use only a portion of said STAT1 and/or USF1 polypeptides provided that they retain their properties of binding to each other, and possibly the property of binding to their respective sites. In a preferred case of the invention, the STAT1 polypeptide is capable of binding to the GAS element (5'-TTCTGATAAA-3') (SEQ ID NO:3) as it is in its activated form (phosphorylated). This phosphorylation of the STAT1 polypeptide can in particular be produced a) naturally, in a cell expressing said polypeptide induced by a cytokine, preferably by interferon γ; b) by the action of a kinase, such as JAK1, or c) chemically, by synthesis.

In a first variation, step d) consists of an indirect measurement, i.e., in this particular case the formation of complexes comprising STAT1, USF1 and a double strand nucleic acid sequence comprising the GAS element (5'-TTCTGATAAA-3') (SEQ ID NO:3) and the E-box (5'-CACGTG-3') is determined. This type of method has been widely described in the literature, is generally based on electrophoretic migration experiments (band shift) and examples thereof are presented in the present application.

In a second variation, step d) consists of a further indirect measurement, i.e., in this case, expression of a nucleic acid sequence coding for all or a portion of a polypeptide is measured, said expression being placed under the control of a promoter comprising at least the GAS element (5'-TTCTGATAAA-3') (SEQ ID NO:3) and the E-box (5'-CACGTG-3') or its complementary sequence.

In a preferred implementation of the invention, said promoter sequence is selected from sequences comprising all or a portion of promoter IV (SEQ ID NO:1) or its complementary sequence.

In accordance with the invention, said nucleic acid sequences the expression of which is measured in step d) can 1) be reporter genes such as the rabbit β globin gene, the luciferase gene or the β lactamase gene, or 2) code for all or a portion of polypeptides with the amino acid sequence of a CIITA factor as described in French patent application 97 04954, and more particularly as defined by SEQ ID NO: 2 (as shown on Table 2). In the latter case, it can be said that they code for all or a portion of the CIITA polypeptide.

In particular, the expression of the nucleic acid sequence can consist of a) measuring the specific messenger RNA expressed from said nucleic acid sequence or b) measuring the polypeptide expressed. Examples of such methods have been widely developed in the literature and the skilled person is capable of implementing them. Examples which can be cited are techniques such as those based on hybridization of labelled oligonucleotide probes the sequence of which is specific for the RNA to be detected, amplification, for example by PCR using primers the sequence of which is specific for said RNA, the technique involving protection against degradation by RNAse, or the use of specific antibodies for all or a portion of the synthesized polypeptide, etc.

In a particular and preferred case of the second variation of the invention, the step for measuring the expression of the nucleic acid sequence is carried out under conditions enabling induction of said expression by a cytokine, more particularly interferon γ.

In a third variation of the invention, step d) consists of direct measurement of the formation of complexes between the STAT1 and USF1 polypeptides, for example using specific antibodies for said complexes or any other suitable means.

The measurement methods proposed in the variations described above are also suitable for the method of the invention presented below.

The invention also provides a method for determining whether a candidate compound is capable of inhibiting expression of a nucleic acid sequence coding for all or a portion of a polypeptide, preferably for all or a portion of the CIITA polypeptide (SEQ ID NO: 2) or for all or a portion of a reporter gene placed under the control of all or a portion of a promoter comprising at least the GAS element (5'-TTCTGATAAA-3') (SEQ ID NO:3) and the E-box (5'-CACGTG-3'), preferably of promoter IV (SEQ ID NO:1), or their respective complementary sequences, comprising the following steps:

(a) providing all or a portion of a STAT1 polypeptide having the property of binding to the USF1 protein and to the GAS element (5'-TTCTGATAAA-3') (SEQ ID NO:3);

(b) providing all or a portion of the USF1 protein having the property of binding to the STAT1 protein and to the E-box (5'-CACGTG-3');

(c) providing a nucleic acid sequence coding for all or a portion of a polypeptide, preferably for all or a portion of the CIITA polypeptide (SEQ ID NO:2) or for all or a portion of a reporter gene, the expression of which is placed under the control of all or a portion of a promoter comprising at least the GAS element (5'-TTCTGATAAA-3') (SEQ ID NO:3) and the E-box (5'-CACGTG-3'), preferably of promoter IV (SEQ ID NO: 1);

(d) bringing said polypeptides as defined in a) and b), said nucleic acid sequence as defined in c) and said candidate compound into contact;

(e) measuring the expression of said nucleic acid sequence; and (f) comparing this measurement with the measurement of the expression of said nucleic acid sequence observed under the same experimental conditions, in particular of activation of expression, in the absence of said candidate compound, a reduction in said expression allowing the conclusion that said candidate compound is capable of inhibiting expression of a nucleic acid sequence coding for all or a portion of a polypeptide, in particular for all or a portion of the CIITA polypeptide or for all or a portion of a reporter gene placed under the control of all or a portion of a promoter comprising at least the GAS element (5'-TTCTGATAAA-3') (SEQ ID NO:3) and the E-box (5'-CACGTG-3'), preferably of a promoter IV (SEQ ID NO: 1).

The invention also provides a method for determining whether a candidate compound is capable of inhibiting activation by a cytokine, more particularly by interferon γ, of expression of a nucleic acid sequence coding for all or a portion of a polypeptide, in particular for all or a portion of the CIITA polypeptide (SEQ ID NO: 2) or for all or a portion of a reporter gene, placed under the control of all or a portion of a promoter comprising at least the GAS element (5'-TTCTGATAAA-3') (SEQ ID NO:3 and the E-box (5'-CACGTG-3'), preferably of a promoter IV (SEQ ID NO: 1), comprising the following steps:

(a) providing a cell line, for example the Me67.8 line, expressing natural and functional STAT1 and USF1 polypeptides;

(b) transfecting said cell line with an expression vector comprising at least one nucleic acid sequence coding for all or a portion of a polypeptide, in particular for all or a portion of the CIITA polypeptide (SEQ ID NO: 2) or for all or a portion of a reporter gene, placed under the control of all or a portion of a promoter comprising at least the GAS element (5'-TTCTGATAAA-3') (SEQ ID NO:3) and the E-box (5'-CACGTG-3'), preferably of a promoter IV (SEQ ID NO: 1);

(c) bringing said cells into contact with a said candidate compound or transfecting the cells with an expression vector enabling expression of a said compound inside said cells, under conditions enabling activation of expression of the nucleic acid sequence by a cytokine, preferably interferon γ;

(d) measuring the expression of said nucleic acid sequence; and (e) comparing this measurement with the measurement of the expression of said nucleic acid sequence observed under the same experimental conditions, in particular of activation of expression, in the absence of said candidate compound, a reduction in said expression allowing the conclusion that said candidate compound is capable of inhibiting activation by a cytokine, more particularly by interferon γ, of the expression of a nucleic acid sequence coding for all or a portion of a polypeptide, in particular for all or a portion of the CIITA polypeptide (SEQ ID NO: 2) or for all or a portion of a reporter gene, placed under the control of all or a portion of a promoter comprising at least the GAS element (5'-TTCTGATAAA-3') (SEQ ID NO:3) and E-box (5'-CACGTG-3'), preferably of a promoter IV (SEQ ID NO: 1).

An expression vector comprising at least one nucleic acid sequence coding for all or a portion of a polypeptide placed under the control of all or a portion of promoter IV comprising the GAS element (5'-TTCTGATAAA-3') (SEQ ID NO:3) and the E-box (5'-CACGTG-3') can in particular consist of a vector as described in French patent application 97 04954 the disclosure of which forms part of the present application.

The invention also concerns methods as defined above for identifying candidate compounds which can inhibit expression of genes coding for MHC class II molecules when this is desired, in particular under conditions for which action is required after induction by a cytokine, more particularly interferon γ.

Numerous diseases, directly or indirectly linked to a problem with expression of genes coding for MHC class II molecules have been described in the literature. Examples which can be cited are diseases such as insulin dependent diabetes, multiple sclerosis, rheumatoid arthritis or lupus erythematosus wherein one of the components could be an over-expression of genes coding for MHC class II molecules.

Other advantages and characteristics of the present invention will become apparent from the following examples illustrated in FIG. 1. However, the invention is not limited to the contents of these examples.

EXAMPLES

Materials & Methods

Cells

The cell lines Me67.8 (melanoma) and THP1 (monocyte) were cultivated in RPMI-1640 medium. Lines 2FTGH (fibrosarcoma) and U3A (2FTGH line expressing no STAT1) were cultivated in modified Dulbecco medium. The media were supplemented with 10% foetal calf serum, 10 U/ml of penicillin, 10 mg/ml of streptomycin and 2 mM of glutamine. Incubations were carried out at 37° C. in 5% $CO_2$.

Reporter Genes

Expression of reporter genes was measured by quantitative RT-PCR as described by SPENSER et al., PCR Meth Appli. 1, 164–170. Transfections, RNA preparation and RT-PCR analyses were carried out as previously described (MUHLETHALER-MOTTET et al., 1997, EMBO J., 16, 2851–2860). The plasmid PIV-308 comprises the −308 to +75 fragment of the region flanking the promoter IV of the CIITA gene sub cloned downstream of the gene coding for the rabbit beta globulin of the pGβG(+) plasmid. The activity of the promoter was measured by PhosphoImager.

RNAse Degradation and Protection Assays.

The assays were carried out on 10 μg of RNA by reaction using the technique described by STEIMLE et al., 1993, Cell, 75, 135–146.

Oligonucleotides Used.

NGE:

5'-GGCCAGGGATTGGGATGCGAGTTCTGATAAA GCAGGTGGTGGCCACAG-3'(SEQ ID NO:4);

E: 5'gggAAAGCACGTCCTGGCC-3'(SEQ ID NO:5)

Analysis of Electrophoretic Mobility (EMSA)

The cells used were stimulated or not stimulated by interferon γ (500 U/ml) for 30 min before preparing nuclear extracts using the method described by HARROCH et al., 1994, EMBO J., 13, 1942–1949.

The oligonucleotides, radiolabelled at one of their ends by adding [γ-32P]ATP, were hybridized to their complementary sequence and purified by polyacrylamide gel electrophoresis to obtain labelled double strand DNA probes corresponding to all or a portion of the promoter IV of CIITA.

To study the binding of protein factors to the NGE probe, 6 μg of proteins extracted from cell nuclei were mixed with $2 \times 10^4$ cpm of DNA probe, 1.25 μg of poly (dI) (dC) (Pharmacia), and 0.5 μg of single strand E. Coli DNA with or without a competitor, in a final volume of 20 μl [20 mM Tris-HC 1 pH 7.9, 50 mM NaCl, 1 mM EDTA, 5% (v/v) glycerol, 5 mM dithiothreitol, 1 mM spermine and 100 μg of BSA]. The conditions for binding the factors to the G probe were identical except for: no poly(dI)(dC), no E coli DNA.

The purified and activated recombinant STAT1 protein and the purified and recombinant USF1 protein were used under identical conditions.

After adding the radiolabelled nucleic probe, the mixture was incubated for 30 minutes at 20° C.

For the "supershift" experiments, the antibodies were added and the mixture was left at 4° C. for 20 minutes before carrying out gel electrophoresis on 5% polyacrylamide. After drying, the gel was autoradiographed. The results were determined by PhosphoImager.

Example 1

Demonstration of Two Types of Complex Which Can Form in the GAS/E-box Region.

In order to study the DNA/protein complexes which can form in the region comprising the GAS/E-box cis regulating elements of promoter IV inducible by interferon γ which the Applicant has previously identified (MUHLETHALER-MOTTET et al., 1997, EMBO J., 16, 2851–2860), electrophoretic mobility tests were carried out using DNA probes covering this region (NGE) and with the nuclear extract from Me67.8 cells, after or without induction by interferon γ.

With the nuclear extract prepared from non stimulated cells, it was seen that a complex, denoted L for "lower", was formed between the DNA probe and at least one protein present in the nuclear extract.

With the nuclear extract prepared from cells stimulated by interferon γ, it was seen that another complex was formed, denoted U for "upper", which had a lower electrophoretic mobility.

In order to study the specificity and the DNA binding site of each of the complexes which had been identified, we carried out competition experiments in the presence of specific probes for the GAS element (G) and the E-box (E). The results showed that the L complex was disrupted only by the competing probe E, whether the nuclear extracts originated from unstimulated cells or from interferon γ-stimulated cells. In contrast, formation of the U complex was inhibited by competing probes G and E. These results indicate that the L complex involves a protein capable of binding to the E-box, which is present in non stimulated cells, and a new complex can form after stimulation by interferon γ. Moreover, directed mutagenesis experiments carried on the GAS and E-box elements have also shown that binding of this U complex to DNA is possible only in the presence of wild GAS and E-box sequences.

It is concluded from these experiments that the U complex is formed from at least one factor which is capable of binding to the E-box and a protein activated by interferon γ which binds to the GAS element. A possible candidate for this second protein factor is the STAT1 protein (DECKER et al., 1991, EMBO J., 10, 927–932).

Example 2

In order to evaluate directly the role of STAT1 in regulating the expression of the CIITA gene after activation by interferon γ, the induction capacity of the CIITA gene was studied in a cell line which was deficient for STAT1 (U3A) and in a cell line expressing STAT1 (2FTGH) under conditions of activation by interferon γ.

In contrast to that observed for the 2FTGH line, in the U3A line, expression of CIITA messenger RNA or activation of the CIITA promoter IV were not induced by the cytokine, as shown by RNAse protection experiments and analysis of the promoter function by constructing reporter genes expressed under the control of the promoter to be analysed.

The results showed that STAT1 controls the activation of the CIITA promoter IV by interferon γ. These results agree with the work of MERAZ et al., 1996, Cell, 84, 431–442 which shows that CIITA messenger RNA cannot be induced by interferon γ in macrophages from STAT−/−mice.

In order to analyse the role of STAT1 in CIITA promoter IV and its presence in the U complex, said protein complex, associated with the labelled NGE probe, was analysed by supershift with monoclonal antibodies specific for STAT1. While non specific monoclonal antibodies have no effect on the electrophoretic migration of DNA/U protein complexes, anti-STAT1 monoclonal antibodies considerably retarded the migration of the U complex, even at high dilutions (1/2000), while migration of the L complex remained unchanged. This confirms that the STAT1 protein is a component of the U complex.

Example 3

Functional tests demonstrated the major role played by the E-box during induction by interferon γ. The nucleic acid sequence of the E-box of the CIITA promoter IV has the consensus sequence CACGTG previously described as a helix/loop/helix/leucine zipper protein DNA binding site.

The use of antibodies specific for factor USF1 demonstrated the presence of this factor in U and L protein complexes. In order to confirm that the USF1 factor is capable of binding to the CIITA promoter IV, EMSA experiments were carried out in the presence of USF1 recombinant proteins. The results showed that the USF1 protein is effectively present in the U and L complexes and specifically binds to the CIITA promoter IV.

Example 4

We then analysed whether STAT1 and USF1 proteins formed the U complex co-operatively after induction by interferon γ. To this end, EMSA analyses demonstrated that in contrast to the USF1 recombinant factor which can alone bind to the radiolabelled NGE probe, the STAT1 factor cannot bind to the same probe by itself. Further, adding increasing quantities of activated STAT1 to a given quantity of USF1 in the presence of an excess of free NGE probe encouraged the formation of STAT1/USF1 complexes rather than binding of USF1 alone. The quantity of probe associated with the two factors showed that binding of STAT1 and USF1 was carried out co-operatively since the quantities of probe bound to said complex (17%) was about twice as high as the sum of the probe bound to the USF1 factor alone (7.6%) and to the STAT1 factor alone (0%).

This co-operative binding was also observed with nuclear extracts from non stimulated Me67.8 cells and activated recombinant STAT1 factor. The complexes formed with the recombinant proteins had the same electrophoretic migration profiles as those obtained with nuclear extracts of Me67.8 cells stimulated by interferon γ.

TABLE 1

```
gggagaagt cagaggtaac cttgccccct ccctcaattc cagatgagga aattcaggcc   60
tgaaaaggga aagtgaccac ctcaaagtct catgccttgg aggacccagc aggaatccaa  120
gacctctgaa aaggaccggc agggctcttg ccacggctgg gggtgtggtc atggtaacac  180
aggttttcca tccatggaag gtacctgagg gattttctct tcctccctag ggccagcatc  240
agaggagtga atagctcagt tagctcatct caggggccat gtgccctcgg aggtggtttg  300
ccactttcac ggttggactg agttggagag aaacagagac ccacccaggg gtggggacaa  360
gctccctgca actcaggact tgcagatcac ttgcccaagt ggctccctag ctcctggctc  420
ctggcccggg gcctgggact ctccccgaag tggggctggc cactgtgagg aaccgactgg  480
aggcagggac ctcttggatg ccccaggcag ttgggatgcc acttctgata aagcacgtgg  540
tggccacagt aggtgcttgg ttgctccaca gcctggcccg agctcagcgc tgcagaaaga  600
aagtgaaagg gaaaaagaac tgcggggagg cggggaggta ggatgaccag cggacgagct  660
gcca                                                              664
```

TABLE 2

| | | | | | |
|---|---|---|---|---|---|
| cagacttgcc | gcggccccag | agctggcggg | agggagaggc | caccagcagc | gcgcgcggga | 60 |
| gcccggggaa | cagcggcagc | tcacagtgtg | ccaccatgga | gttggggccc | ctagaaggtg | 120 |
| gctacctgga | gcttcttaac | agcgatgctg | accccctgtg | cctctaccac | ttctatgacc | 180 |
| agatggacct | ggctggagaa | gaagagattg | agctctactc | agaacccgac | acagacacca | 240 |
| tcaactgcga | ccagttcagc | aggctgttgt | gtgacatgga | aggtgatgaa | gagaccaggg | 300 |
| aggcttatgc | caatatcgcg | gaactggacc | agtatgtctt | ccaggactcc | agctggagg | 360 |
| gcctgagcaa | ggacattttc | aagcacatag | gaccagatga | agtgatcggt | gagagtatgg | 420 |
| agatgccagc | agaagttggg | cagaaaagtc | agaaaagacc | cttcccagag | gagcttccgg | 480 |
| cagacctgaa | gcactggaag | ccagctgagc | ccccactgt | ggtgactggc | agtctcctag | 540 |
| tgggaccagt | gagcgactgc | tccaccctgc | cctgcctgcc | actgcctgcg | ctgttcaacc | 600 |
| aggagccagc | ctccggccag | atgcgcctgg | agaaaaccga | ccagattccc | atgccttttct | 660 |
| ccagttcctc | gttgagctgc | ctgaatctcc | ctgagggacc | catccagttt | gtccccacca | 720 |
| tctccactct | gccccatggg | ctctggcaaa | tctctgaggc | tggaacaggg | gtctccagta | 780 |
| tattcatcta | ccatggtgag | gtgccccagg | ccagccaagt | acccctccc | agtggattca | 840 |
| ctgtccacgg | cctcccaaca | tctccagacc | ggccaggctc | caccagcccc | ttcgctccat | 900 |
| cagccactga | cctgccagc | atgcctgaac | ctgccctgac | ctcccgagca | aacatgacag | 960 |
| agcacaagac | gtcccccacc | caatgcccgg | cagctggaga | ggtctccaac | aagcttccaa | 1020 |
| aatggcctga | gccggtggag | cagttctacc | gctcactgca | ggacacgtat | ggtgccgagc | 1080 |
| ccgcaggccc | ggatggcatc | ctagtggagg | tggatctggt | gcaggccagg | ctggagagga | 1140 |
| gcagcagcaa | gagcctggag | cgggaactgg | ccacccagga | ctgggcagaa | cggcagctgg | 1200 |
| cccaaggagg | cctggctgag | gtgctgttgg | ctgccaagga | gcaccggcgg | ccgcgtgaga | 1260 |
| cacgagtgat | tgctgtgctg | ggcaaagctg | gtcagggcaa | gagctattgg | gctggggcag | 1320 |
| tgagccgggc | ctgggcttgt | ggccggcttc | cccagtacga | cttttgtcttc | tctgtcccct | 1380 |
| gccattgctt | gaaccgtccg | ggggatgcct | atggcctgca | ggatctgctc | ttctccctgg | 1440 |
| gcccacagcc | actcgtggcg | gccgatgagg | ttttcagcca | catcttgaag | agacctgacc | 1500 |
| gcgttctgct | catcctagac | gccttcgagg | agctggaagc | gcaagatggc | ttcctgcaca | 1560 |
| gcacgtgcgg | accggcaccg | gcggagccct | gctccctccg | ggggctgctg | gccggccttt | 1620 |
| tccagaagaa | gctgctccga | ggttgcaccc | tcctcctcac | agcccggccc | cggggccgcc | 1680 |
| tggtccagag | cctgagcaag | gccgacgccc | tatttgagct | gtccggcttc | tccatggagc | 1740 |
| aggcccaggc | atacgtgatg | cgctactttg | agagctcagg | gatgacagag | caccaagaca | 1800 |
| gagccctgac | gctcctccgg | gaccggccac | ttcttctcag | tcacagccac | agccctactt | 1860 |
| tgtgccgggc | agtgtgccag | ctctcagagg | ccctgctgga | gcttggggag | gacgccaagc | 1920 |
| tgccctccac | gctcacggga | ctctatgtcg | gcctgctggg | ccgtgcagcc | ctcgacagcc | 1980 |
| cccccggggc | cctggcagag | ctggccaagc | tggcctggga | gctgggccgc | agacatcaaa | 2040 |
| gtaccctaca | ggaggaccag | ttcccatccg | cagacgtgag | gacctgggcg | atggccaaag | 2100 |
| gcttagtcca | acacccaccg | cgggccgcag | agtccgagct | ggccttcccc | agcttcctcc | 2160 |
| tgcaatgctt | cctgggggcc | ctgtggctgg | ctctgagtgg | cgaaatcaag | gacaaggagc | 2220 |
| tcccgcagta | cctagcattg | accccaagga | agaagaggcc | ctatgacaac | tggctggagg | 2280 |
| gcgtgccacg | ctttctggct | gggctgatct | tccagcctcc | cgcccgctgc | ctgggagccc | 2340 |
| tactcgggcc | atcggcggct | gcctcggtgg | acaggaagca | gaaggtgctt | gcgaggtacc | 2400 |

TABLE 2-continued

```
tgaagcggct gcagccgggg acactgcggg cgcggcagct gcttgagctg ctgcactgcg    2460
cccacgaggc cgaggaggct ggaatttggc agcacgtggt acaggagctc cccggccgcc    2520
tctcttttct gggcacccgc ctcacgcctc ctgatgcaca tgtactgggc aaggccttgg    2580
aggcggcggg ccaagacttc tccctggacc tccgcagcac tggcatttgc ccctctggat    2640
tggggagcct cgtgggactc agctgtgtca cccgtttcag ggctgccttg agcgacacgg    2700
tggcgctgtg ggagtccctg cggcagcatg gggagaccaa gctacttcag gcagcagagg    2760
agaagttcac catcgagcct ttcaaagcca agtccctgaa ggatgtggaa gacctgggaa    2820
agcttgtgca gactcagagg acgagaagtt cctcggaaga cacagctggg gagctccctg    2880
ctgttcggga cctaaagaaa ctggagtttg cgctgggccc tgtctcaggc ccccaggctt    2940
tccccaaact ggtgcggatc ctcacggcct tttcctccct gcagcatctg gacctggatg    3000
cgctgagtga gaacaagatc ggggacgagg gtgtctcgca gctctcagcc accttccccc    3060
agctgaagtc cttggaaacc ctcaatctgt cccagaacaa catcactgac ctgggtgcct    3120
acaaactcgc cgaggccctg ccttcgctcg ctgcatccct gctcaggcta agcttgtaca    3180
ataactgcat ctgcgacgtg ggagccgaga gcttggctcg tgtgcttccg acatggtgt     3240
ccctccgggt gatggacgca agttcacggc tgccggggcc cagcagctcg ctgccagcct    3300
tcggaggtgt cctcatgtgg agacgctggc gatgtggacg cccaccatcc cattcagtgt    3360
ccaggaacac ctgcaacaac aggattcacg gatcagcctg agatgatccc agctgtgctc    3420
tggacaggca tgttctctga ggacactaac cacgctggac cttgaactgg gtacttgtgg    3480
acacagctct tctccaggct gtatcccatg aggcctcagc atcctggcac ccggcccctg    3540
ctggttcagg gttggcccct gcccggctgc ggaatgaacc acatcttgct ctgctgacag    3600
acacaggccc ggctccaggc tcctttagcg cccagttggg tggatgcctg gtggcagctg    3660
cggtccaccc aggagccccg aggccttctc tgaaggacat tgcggacagc cacggccagg    3720
ccagagggag tgacagaggc agccccattc tgcctgccca ggcccctgcc accctgggga    3780
gaaagtactt cttttttttt atttttagac agagtctcac tgttgcccag gctggcgtgc    3840
agtggtgcga tctgggttca ctgcaacctc cgcctcttgg gttcaagcga ttcttctgct    3900
tcagcctccc gagtagctgg gactacaggc acccaccatc atgtctggct aattttcat     3960
ttttagtaga cagggtttt tgccatgttg gccaggctgg tctcaaactc ttgacctcag     4020
gtgatccacc cacctcagcc tcccaaagtg ctggggatta caagcgtgag ccactgcacc    4080
gggccacaga gaaagtactt ctccaccctg ctctccgacc agacaccttg acagggcaca    4140
ccgggcactc agaagacact gatgggcaac ccccagcctg ctaattcccc agattgcaac    4200
aggctgggct tcagtggcag gctgcttttg tctatggac tcaatgcact gacattgttg     4260
gccaaagcca aagctaggcc tggccagatg caccaggccc ttagcaggga aacagctaat    4320
gggacactaa tggggcggtg agaggggaac agactggaag cacagcttca tttcctgtgt    4380
ctttttttcac tacattataa atgtctcttt aatgtcacaa aaaaaaaaaa aaaaaaaaa    4440
a                                                                   4441
```

What is claimed is:

1. A method for determining whether a candidate compound is capable of inhibiting binding between STAT1 and USF1 polypeptides, comprising steps:
   (a) providing all or a portion of the STAT1 polypeptide having the property of binding to the USF1 polypeptide;
   (b) providing all or a portion of the USF1 polypeptide having the property of binding to the STAT1 polypeptide;
   (c) bringing said polypeptides as defined in a) and b) into contact with said candidate compound under conditions which enable binding between the STAT1 and USF1 polypeptides;
   (d) measuring the binding between the STAT1 and USF1 polypeptides; and
   (e) comparing this measurement with that for binding between the STAT1 and USF1 polypeptides observed under the same experimental conditions in the absence of said candidate compound, a reduction in binding allowing the conclusion that said candidate compound is capable of inhibiting binding between the STAT1 and USF1 polypeptides.

2. A method according to claim 1, wherein step d) consists of measuring the formation of complexes comprising STAT1, USF1 and a double strand nucleic acid sequence comprising the GAS element (5'-TTCTGATAAA-3') (SEQ ID NO:3) and the E-box (5'-CACGTG-3').

3. A method according to claim 1, wherein step d) consists of measuring the expression of a nucleic acid sequence coding for all or a portion of a polypeptide, said expression being placed under the control of a promoter sequence comprising the GAS element (5'-TTCTGATAAA-3') (SEQ ID NO:3) and the E-box (5'-CACGTG-3'), or its complementary sequence.

4. A method according to claim 2, or claim 3, wherein said double strand nucleic acid sequence or said promoter sequence respectively comprises all or a portion of the promoter IV (SEQ ID NO:1) or its complementary sequence.

5. A method according to claim 3, wherein said polypeptide is the CIITA polypeptide (SEQ ID NO:2).

6. A method according to claim 3, wherein said polypeptide is the rabbit β globulin polypeptide, luciferase or β lactamase.

7. A method according to claim 3 wherein expression of said nucleic acid sequence is measured under conditions enabling induction of said expression by a cytokine.

8. A method for determining whether a candidate compound is capable of inhibiting expression of a nucleic acid sequence coding for all or a portion of a polypeptide placed under the control of all or a portion of a promoter comprising the GAS element (5'-TTCTGATAAA-3') (SEQ ID NO:3) and the E-box (5'-CACGTG-3'), comprising the following steps:
   (a) providing all or a portion of the STAT1 polypeptide having the property of binding to the USF1 protein and to the GAS element (5'-TTCTGATAAA-3')(SEQ ID No:3);
   (b) providing all or a portion of the USF1 polypeptide having the property of binding to the STAT1 protein and to the E-box (5'-CACGTG-3');
   (c) providing a nucleic acid sequence coding for all or a portion of a polypeptide the expression of which is placed under the control of all or a portion of a promoter comprising the GAS element (5'-TTCTGATAAA-3') (SEQ ID NO:3) and the E-box (5'-CACGTG-3');
   (d) bringing said polypeptides as defined in a) and b), said nucleic acid sequence as defined in c) and said candidate compound into contact;
   (e) measuring the expression of said nucleic acid sequence; and
   (f) comparing this measurement with that of the expression of said nucleic acid sequence observed under the same experimental conditions, including conditions of activation of expression, in the absence of said candidate compound, a reduction in said expression allowing the conclusion that said candidate compound is capable of inhibiting expression of a nucleic acid sequence coding for all or a portion of a polypeptide placed under the control of all or a portion of a promoter comprising the GAS element (5'-TTCTGATAAA-3') (SEQ ID NO:3) and the E-box (5'-CACGTG-3').

9. A method according to claim 8, wherein said nucleic acid sequence codes for all or a portion of the CIITA polypeptide (SEQ ID NO:2).

10. A method according to claim 8, wherein said nucleic acid sequence codes for all or a portion of a reporter gene.

11. A method according to claim 8, wherein said promoter comprising the GAS element (5'-TTCTGATAAA-3') (SEQ ID NO:3) and the E-box (5'-CACGTG-3') is promoter IV (SEQ ID NO:1).

12. A method according to claim 8, wherein expression of said nucleic acid sequence is measured by measuring the specific messenger RNA expressed from said nucleic acid sequence.

13. A method according to claim 8, wherein expression of said nucleic acid sequence is measured by measuring the polypeptide expressed.

14. A method according to claim 7, wherein said cytokine is interferon γ.

15. A method according to claim 10, wherein said reporter gene is rabbit β globulin, luciferase or β lactamase.

* * * * *

UNITED STATES PATENT AND TRADEMARK OFFICE
CERTIFICATE OF CORRECTION

PATENT NO. : 6,379,894 B1
DATED : April 30, 2002
INVENTOR(S) : Bernard Mach

It is certified that error appears in the above-identified patent and that said Letters Patent is hereby corrected as shown below:

<u>Title page, Item [54] and Column 1, line 2,</u>
Title, change "BINDING" to -- FIXING --.

Item [73], Assignee, change "Novimaune" to -- Novimmune --.
Item [57], delete entire ABSTRACT, and insert -- Disclosed is a method for determining whether a candidate compound is capable of inhibiting fixing between STAT1 and USF1 polypeptides. -- (as Amended)

<u>Column 3,</u>
Line 1, change "y" to -- γ --.
Line 23, change "y" to -- γ --.

<u>Column 4,</u>
Line 27, change "y" to -- γ --.

<u>Column 5,</u>
Line 59, delete "STATS" and insert -- STAT1. --

Signed and Sealed this

Eighth Day of October, 2002

*Attest:*

JAMES E. ROGAN
*Attesting Officer*  *Director of the United States Patent and Trademark Office*

UNITED STATES PATENT AND TRADEMARK OFFICE
CERTIFICATE OF CORRECTION

PATENT NO.    : 6,379,894 B1
DATED         : April 30, 2002
INVENTOR(S)   : Bernard Mach It is certified that error appears in the above-identified patent and that said Letters Patent is hereby corrected as shown below:

<u>Title page,</u>
Item [54], delete "METHOD FOR SCREENING COMPOUNDS CAPABLE OF INHIBITING BINDING BETWEEN THE TRANSCRIPTION FACTOR OF STAT1 AND THE TRANSCRIPTION FACTOR OF USF1" and insert
-- METHOD FOR SCREENING COMPOUNDS CAPABLE OF INHIBITING FIXING BETWEEN THE STAT1 TRANSCRIPTION FACTOR AND THE USF1 TRANSCRIPTION FACTOR --

Signed and Sealed this

Twenty-fourth Day of December, 2002

JAMES E. ROGAN
*Director of the United States Patent and Trademark Office*